United States Patent [19]

Rademacher et al.

[11] Patent Number: 4,689,412

[45] Date of Patent: Aug. 25, 1987

[54] METHOD FOR PREPARING LACTAMS HAVING 8 TO 15 CARBON ATOMS FROM THE CORRESPONDING OXIMES

[75] Inventors: Hans Rademacher, Marl; Heinz-Werner Voges, Dorsten, both of Fed. Rep. of Germany

[73] Assignee: Huls Aktiengesellschaft, Marl, Fed. Rep. of Germany

[21] Appl. No.: 919,466

[22] Filed: Oct. 16, 1986

[30] Foreign Application Priority Data

Nov. 2, 1985 [DE] Fed. Rep. of Germany ....... 3538859

[51] Int. Cl.$^4$ ............................................ C07D 201/04
[52] U.S. Cl. .................................. 540/464; 540/535; 540/540
[58] Field of Search .................. 540/464, 535, 540

[56] References Cited

U.S. PATENT DOCUMENTS 3,228,527 10/1966 Yura et al. ..................... 540/535

*Primary Examiner*—Robert T. Bond
*Attorney, Agent, or Firm*—Quaintance, Murphy & Presta

[57] ABSTRACT

The present invention is a process for preparing lactams having 8 to 15 carbon atoms by the Beckmann rearrangement of the corresponding oximes in a solution of an organic solvent by means of 0.5 to 10% by weight referred to the oxime of an acid derivative acting as a catalyst. The anhydrides of organic sulfonic acids or of sulfuric acid half esters or mixed anhydrides of organic sulfonic acid and anhydrides of sulfuric acid half esters are used as the catalysts.

20 Claims, No Drawings

METHOD FOR PREPARING LACTAMS HAVING 8 TO 15 CARBON ATOMS FROM THE CORRESPONDING OXIMES

Cross Reference to a Related Application

Applicants claim priority under 35 USC 119 for application P 35 38 859.5, filed November 2, 1985, in the Patent Office cf the Federal Republic of Germany.

BACKGROUND OF THE INVENTION

The field of the invention is the production of lactams from their corresponding oximes by the Beckmann rearrangement and the present invention is particularly concerned with the production of lactams by the Beckmann rearrangement using anhydrides of sulfuric acid half esters, anhydrides of sulfonic acids or mixtures thereof as catalysts.

The preparation of lactams by oximating cycloaliphatic ketones and by the subsequent Beckmann rearrangement is known and the state of the art may be ascertained by reference to British Pat. No. 1,467,565 and US Patents 3,931,255 and 3,462,417, the disclosures of which are incorporated by reference into the present application.

The Beckmann rearrangement typically is carried out on a large industrial scale by means of concentrated sulfuric acid or oleum. In this procedure, the material being rearranged is employed in a molar amount exceeding that of the oxime. Accordingly this method suffers from the drawback that appreciable quantities of diluted sulfuric acid are processed or separated. The preparation of epsilon-caprolactam from cyclohexanonoxime is described in Ullmann's ENZYKLOPAEDIE DER TECHNISCHEN CHEMIE, Vol. 9, pp 100, 175, and the preparation of lauryllactam from cyclododecanonoxime is described by K. Weissermel and H. J. Arpe in the tome INDUSTRIELLE ORGANISCHE CHEMIE, Chemie publishers, Weinheim 1976, the disclosures of which are incorporated by reference into the present application.

It is known furthermore to rearrange alicyclic ketoximes having 9 to 14 carbon atoms in the ring with catalytic means, using merely 0.5 to 5% by weight referred to the amount of the oxime of an acid chloride such as thionyl chloride, phosphorus oxychloride, phosphorus pentachloride, benzene sulfochloride as disclosed in British Pat. No. 1,467,565.

Since these catalysts are used in substantially lesser amounts, their separation and processing inherently does not require the expenditure demanded for instance when sulfuric acid or oleum is used as the rearranging agent, as disclosed in British Pat. No. 1,467,565.

However, the method of British Pat. No. 1,467,565 entails an appreciable drawback. The lactam obtained by this procedure contains slight though not trivial amounts of chlorine, about 100 to 200 ppm. Such contaminated lactams cannot be used in the production of the corresponding polyamides. Especially as regards the further processing of the polyamides into molded bodies, the chlorinated contaminants damage the apparatus and also damage the polymers at the conventional treatment temperatures, especially because of the hydrogen chloride formed.

SUMMARY OF THE INVENTION

It is therefore an object of the present invention to provide catalysts which can be employed in the known low proportions of 0.5 to 10% by weight referred to the oximes and which upon termination of the rearrangement can be easily removed and which most of all are free of chlorine and other halogens having reactive bonds, that is, those which leave no halogen residues in the lactam. The solution to the problem is therefore to prepare lactams free of halogens which are suitable for the problem-free manufacture of polyamides and the molded bodies made therefrom.

These lactams free of halogens are achieved when sulfonic acid anhydrides, anhydrides of sulfuric acid half esters, or a mixture of the anhydrides of sulfonic acids and anhydrides of sulfuric acid half esters are used as the catalysts.

The anhydrides used as catalysts are used in proportions of about 0.5 to 10% by weight and preferably in proportions of 0.5 to 5 and in particular in proportions of 1 to 3% by weight referred to the oximes used.

The rearrangement is carried out in organic solvents. Suitable solvents are those which adequately dissolve both the oxime and the lactam at the conditions of the reactions and have a high enough corresponding boiling point and remain unchanged during the rearrangement. The concentration of the oxime in the solvent is about 2 to 40% by weight.

As a rule, the temperature of the rearrangement reaction is between about 60° and 140° C., especially between 80° and 120° C. The reaction takes place very rapidly, generally between 1 and 20 minutes, especially between 1 and 10 minutes.

DESCRIPTION OF THE PREFERRED EMBODIMENTS

Suitable anhydrides of sulfonic acids are those alkyl-, halogenoalkyl-, aryl-, or aralkyl sulfonic acids having the general formula:

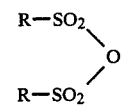

where R is an alkyl group with 1 to 6 carbon atoms, in particular 1 to 2 carbon atoms or a halogenoalkyl group with 1 to 6, in particular 1 to 2 carbon atoms, the hydrogen atoms being replaceable in part or in whole by halogens.

The aryl groups are suitably phenyl, naphthyl or substituted phenyl or substituted naphthyl and the aralkyl groups suitably contain one or more alkyl groups with 1 to 6, in particular 1 to 2 carbon atoms.

Suitable sulfonic acid anhydrides having alkyl groups illustratively are n-propane sulfonic acid anhydride, butane sulfonic acid anhydride pr hexane sulfonic acid anhydride.

Methane sulfonic acid anhydride and ethane sulfonic acid anhydride are especially well suited.

Illustrative sulfonic acid anhydrides having halogenoalkyl groups are chloromethane sulfonic acid anhydride, fluoromethane sulfonic acid anhydride, especially trichloromethane sulfonic acid anhydride and trifluoromethane sulfonic acid anhydride.

Suitable sulfonic acid anhydrides of aromatic sulfonic acids are toluene sulfonic acid anhydride, o-, m- and p-chlorobenzene sulfonic acid anhydride, o-, m- and p-nitrobenzene sulfonic acid anhydride, in particular benzene sulfonic acid anhydride and naphthalin sulfonic acid anhydride.

The sulfonic acid anhydrides are produced by known methods as disclosed in Organic Synthesis Coll., Vol. IV, p 940, 1963. Advantageously the sulfonic acid anhydrides also are used in the form of reactive solutions provided that they are previously rid of halogenated reagents, for instance thionyl chloride.

Anhydrides of sulfuric acid half esters useful in the present invention belong to the general formula

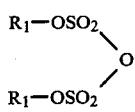

where the two groups $R_1$ can also close into a ring. Further, $R_1$ is an alkyl or halogenoalkyl group as described above in relation to the sulfonic acid anhydrides, namely an alkyl having 1 to 6 carbon atoms, in particular 1 carbon atom, or a halogenoalkyl having 1 to 6 carbon atoms, in particular 1 carbon atom, the hydrogen atoms being replaceable in whole or in part by halogens.

Suitable sulfuric acid half ester anhydrides having alkyl groups illustratively are diethylpyrosulfate, dipropylpyrosulfate, dibutylpyrosulfate, in particular dimethylpyrosulfate. Illustrative sulfuric acid half ester anhydrides with halogenoalkyl groups are bischloromethylpyrosulfate, bisfluoromethylpyrosulfate and bisdichloromethylpyrosulfate, in particular bistrifluoromethylpyrosulfate and bistrichloromethylpyrosulfate.

The anhydrides of sulfuric acid semi esters are prepared by known methods as disclosed in Matschinskaja, Below & Ussow, Z. obsc. Chim. 17, (1947, p. 2295, and Chemical Abstracts 1948, p. 4918.

Mixed anhydrides of sulfonic acids and sulfuric acid semi esters are defined by the general formula

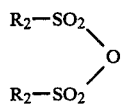

where the $R_2$ groups are the same or different or can be closed into a ring. $R_2$ furthermore is suitably an alkyl, halogenoalkyl or aromatic group, namely an alkyl having 1 to 6 carbon atoms, in particular 1 carbon atom, where the hydrogen atoms can be replaced in whole or in part by halogens. Phenyl, naphthyl, substituted phenyl or substituted naphthyl act as aryl groups and suitable aralkyl groups are those which contain one or more alkyl groups having 1 to 6 carbon atoms, in particular 1 carbon atom. Suitable anhydrides with alkyl groups illustratively are the anhydrides of methane sulfonic acid with sulfuric acid monoethyl-, especially monomethylesters. Suitable anhydrides having halogenoalkyl groups illustratively are the anhydrides of trifluoromethane sulfonic acid with sulfuric acid mono-methyl-, chloromethyl- and trichloromethyl-esters. Suitable anhydrides having aryl groups illustratively are the anhydrides of benzene sulfonic acid with sulfuric acid monomethyl-, trifluoromethyl-, ethyl-, and butyl-esters. Carbyl sulfate is included in the cyclic compounds.

The mixed anhydrides are prepared for instance by the method of British Pat. No. 666,154.

The sulfonic acid anhydrides are especially well suited because they are most easily obtained in the industry. They are, furthermore, especially well suited because they can be used in slight quantities and are very economical.

The oximes of cycloaliphatic ketones having 8 to 15 carbon atoms are useful, but advantageously the higher carbon atom ketones having 10 to 14 carbon atoms are used, for instance cyclododecanonoxime, cycloundecanonoxime, cyclodecanonoxime, in particular cycloundecanonoxime and cyclododecanonoxime.

Examples of the lactams having 8 to 15 carbon atoms produced by the present invention include lauryllactam, decanolactam, undecanolactam, octanolactam, tridecanolactam.

The Beckmann rearrangement is carried out in organic solvents. Suitable solvents are those which adequately dissolve both the oxime and the lactam at the conditions of the reactions and have a high enough corresponding boiling point to remain unchanged during the rearrangement. Accordingly, both aliphatic and cycloaliphatic or aromatic hydrocarbons are conventionally suited.

In particular, toluene and isopropylcyclohexane are especially well suited. Such solvents make it possible to remove the heat of reaction by hot cooling (at the boiling point) at normal or reduced pressure.

The temperature of the Beckmann rearrangement reaction is between about 60° and 140° C., especially between 80° and 120° C. The reaction takes place very rapidly, generally between 1 and 20 minutes, especially between 1 and 10 minutes.

As a rule, the reaction is carried out so that the above mentioned oxime solution is combined with the catalyst. Appropriately the catalyst is introduced as a solution or dispersion into the same solvent. Typically the reaction takes place in high exothermal manner. The heat of reaction as a rule is drained away by hot cooling at reflux. Where required, the hot cooling is supplemented or replaced by another cooling method by heat exchange.

The end of the Beckmann rearrangement is determined by the temperature drop.

The still warm reaction solution is washed until neutral. When called for, post-treatment may be applied with aqueous alkaline means, for instance an alkali hydroxide solution.

Once the solution is rid of the catalyst, the lactam is obtained in conventional manner by distillation or crystallization. When appropriate, so-called intermediate boiling substances may be used as described in West German Published Application No. 1,545,696; 1,795,575; and U.S. Pat. No. 3,431,255, during the fractionated distillation of the lactam solution.

SPECIFIC EXAMPLES Comparison Example (according to British Pat. No. 1,467,565)

40 g of cyclododecanonoxime are dissolved in 160 g of toluene in a flask provided with a thermometer, a stirrer and reflux condenser, and 0.8 g of thionyl chloride are added to the solution heated to 95° C. The rearrangement reaction takes place after a short time, indicating that the reaction mixture boils with reflux because of the high dissipation of heat. The reaction is terminated after 5 minutes as indicated by the reduction in boiling point and lastly by the temperature drop. A sample taken from the reaction mixture is analyzed, for instance by gas chromatography. It is found that the sample no longer contains any oxime, that is, the oxime reaction is 100%. The lauryllactam concentration in the sample corresponds to a lauryllactam yield of 98%.

After being cooled to 90° C., the reaction solution is washed several times until the wash water shows neutral reactions. Half of the reaction solution is allowed to cool to room temperature. The lactam crystallizing thereby is isolated and again recrystallized from toluene. The lactam so obtained has a chlorine content of 110 ppm. The other half of the reaction solution washed until neutral is then processed by distillation. First the toluene and the small proportions of dissolved water are distilled off at normal pressure and thereupon the lactam is distilled off at a pressure of 500 Pa. The chlorine content of the lactam obtained in this manner (the main fraction) is at least 100 ppm and may rise to 200 ppm.

EXAMPLE 1

40 g of cyclododecanonoxime are dissolved in 160 g of toluene in a flask equipped with a thermometer, a stirrer and a reflux condenser, and 0.8 g of benzene sulfonic acid anhydride dissolved in 10 g of toluene are added to the solution heated to 95° C. High heat generation is observed at once, as a result of which the solution boils with reflux. The reaction is over after five minutes as noted by the temperature drop. Analysis by gas chromatography shows oxime reaction of 100% and a lactam yield exceeding 99%. The still warm reaction solution is washed until neutral with warm water to remove the catalyst. The lauryllactam obtained by distillation is free of chlorine contaminants.

EXAMPLES 2 THROUGH 11

Similarly to the procedure in Example 1, 40 g of cyclododecanonoxime are dissolved in 200 ml of isopropylcyclohexane and are treated at 100° C. with the particular type and amount of catalyst in about 10 ml of isopropylcyclohexane as indicated in the following Table. The distillation purified lactams are halogen free.

and a decanolactam yield of 94.7%. The decanolactam obtained by distillation following the water wash is halogen free.

EXAMPLE 13

Similar to Example 1, 40 g of cycloundecanonoxime are dissolved in 200 ml of isopropylcyclohexane and are rearranged with 0.8 g of benzene sulfonic acid anhydride. Gas chromatography shows there is full oxime reaction and a yield of undecanolactam of 97.6%. The undecanolactam obtained by distillation after the water wash is halogen free.

EXAMPLE 14 (Continuous Operation)

2.5 liters (=2 kg) an hour of a 100° C. solution of 25% by weight of cyclododecanonoxime in isopropylcyclohexane and 47 ml of a hot solution of 20% by weight benzene sulfonic acid anhydride in isopropylcyclohexane (corresponding to 1.5% by weight of catalyst referred to the oxime) are pumped through a reaction tube 4,000 mm long and 10 mm in diameter which is thermostatted at 100° C. The reactor discharge is washed in a cascade of agitation vessels in continuous manner first with aqueous sodium hydroxide and then twice with water. Each hour 2.48 liters of product solution containing 480 g of lauryllactam (96% yield) are obtained. Gas chromatography does not show any oxime (<0.1%). After the solvent is removed, the lactam is distilled. It is free of chlorine contaminants.

We claim:

1. In a process for preparing lactams having 8 to 15 carbon atoms by the Beckmann rearrangement of oximes of cycloaliphatic ketones having 8 to 15 carbon atoms in the presence of a catalyst and in the presence of an organic solvent in which both said oximes and lactams are soluble, said solvent remaining unchanged during said rearrangement to form a solution of said oximes and catalyst, the improvement comprising:

said catalyst having a concentration of about 0.5 to 10

TABLE

| Example | Catalyst | Amount in % by weight referred to the oxime | Reaction duration in minutes | oxime conversion % | Lactam Selectivity °C. |
|---|---|---|---|---|---|
| 2 | methane sulfonic acid anhydride | 4 | 3 | 99.1 | 98.5 |
| 3 | trifluoromethane sulfonic acid anhydride | 3 | 3 | 100 | 99.2 |
| 4 | benzene sulfonic acid anhydride | 2 | 2 | 99.9 | 99.2 |
| 5 | p-toluene sulfonic acid anhydride | 10 | 10 | 85.1 | 90.9 |
| 6 | p-chlorobenzene sulfonic acid anhydride | 2 | 5 | 99.7 | 99.1 |
| 7 | p-nitrobenzene sulfonic acid anhydride | 0.5 | 5 | 97.3 | 98.5 |
| 8 | dimethylpyrosulfate | 3 | 3 | 99.7 | 97.9 |
| 9 | C$_6$H$_5$—SO$_2$—O—SO$_2$—O—nC$_4$H$_9$ | 5 | 3 | 100 | 98.3 |
| 10 | CF$_3$—SO$_2$—O—SO$_2$—O—C$_{12}$H$_{25}$ | 5 | 5 | 100 | 98.6 |
| 11 | Carbylsulfate | 10 | 5 | 97.3 | 98.4 |

EXAMPLE 12

As in Example 1, 40 g of cyclododecanonoxime are dissolved in 200 ml of isopropylcyclohexane and then treated at 100° C. with 0.8 g of benzene sulfonic acid anhydride dissolved in 10 ml of isopropylcyclohexane. Gas chromatography shows an oxime reaction of 100% percent by weight of said catalyst referred to the weight of said oximes and said catalyst is selected from the group consisting of anhydrides of organic solfonic acids, anhydrides of sulfuric acid half esters and mixtures thereof.

2. The process of claim 1, wherein said catalyst has a concentration of 1 to 3 percent by weight.

3. The process of claim 1, wherein said catalyst is the anhydride of benzene sulfonic acid.

4. The process of claim 1, wherein said catalyst is the anhydride of methane sulfonic acid.

5. The process of claim 1, wherein said rearrangement is carried out at temperatures up to 140° C.

6. The process of claim 1, wherein said rearrangement is carried out at temperatures between about 60 and 140° C.

7. A process for preparing lactams by the Beckmann rearrangement of oximes in the presence of a catalyst comprising:
  (a) mixing oximes of cycloaliphatic ketones having 8 to 15 carbon atoms with about 0.5 to 10 percent by weight of said catalyst based on the weight of said oximes said catalyst selected from the group consisting of anhydrides of organic sulfonic acids, anhydrides of sulfonic acid half esters and mixtures thereof in the presence of an organic solvent in which both said oximes and lactams are soluble, said solvent remaining unchanged during said rearrangement to form a solution of said oximes and catalyst;
  (b) reacting said solution of oximes and catalyst at a temperature of about 60° to 140° C. to carry out said rearrangement of said oximes to the corresponding lactams having 8 to 15 carbon atoms to form a reaction solution;
  (c) separating said catalyst from lactams and organic solvent; and
  (d) separating said lactams from said organic solvent.

8. The process of claim 7, wherein step (c) is carried out by water washing from reaction solution.

9. The process of claim 8, wherein step (d) is carried out by distillation.

10. The process of claim 9, wherein said oximes are selected from the group consisting of cyclododecanonoxime, cycloundecanonoxime and cyclodecanonoxime.

11. The process of claim 10, wherein said lactams are selected from the group consisting of lauryllactam, decanolactam, octanolactam, tridecanolactam and undecanolactam.

12. The process of claim 1, wherein said catalyst has a concentration of 0.5 to 5% by weight.

13. The process of claim 1, wherein said oximes have a concentration in said solvent of 2 to 40% by weight.

14. The process of claim 1, wherein said rearrangement is carried out at temperatures between about 80° and 120° C.

15. The process of claim 5, wherein said rearrangement is carried out between 1 and 20 minutes.

16. The process of claim 14, wherein said rearrangement is carried out between 1 and 10 minutes.

17. The process of claim 7 wherein, said catalyst has a concentration of 0.5 to 5% by weight.

18. The process of claim 7, wherein said oximes have a concentration in said solvent of 2 to 40% by weight.

19. The process of claim 7 wherein, said rearrangement is carried out at temperatures between about 80 and 120° C.

20. The process of claim 19, wherein said rearrangement is carried out between 1 and 10 minutes.

* * * * *